United States Patent [19]
Petrov et al.

[11] Patent Number: 5,481,028
[45] Date of Patent: Jan. 2, 1996

[54] LEWIS ACID CATALYZED CONJUGATED IODOFLUORINATION OF FLUOROOLEFINS

[75] Inventors: Viacheslav A. Petrov; Carl G. Krespan, both of Wilmington, Del.

[73] Assignee: E. I. Du Pont de Nemours and Company, Wilmington, Del.

[21] Appl. No.: 290,326

[22] Filed: Aug. 12, 1994

Related U.S. Application Data

[63] Continuation-in-part of Ser. No. 99,679, Jul. 29, 1993, abandoned.

[51] Int. Cl.$^6$ ............ C07C 69/66; C07C 43/00; C07C 17/08
[52] U.S. Cl. ............ 560/184; 562/833; 568/684; 570/165; 570/166; 570/168
[58] Field of Search ............ 570/137, 161, 570/165, 174, 166, 168, 184; 568/684; 560/184; 562/833

[56] References Cited

U.S. PATENT DOCUMENTS

| | | | |
|---|---|---|---|
| 3,132,185 | 5/1964 | Parsons | 260/653 |
| 3,283,020 | 11/1966 | Parsons | 260/653 |
| 3,829,512 | 8/1974 | Millauer | 260/653.6 |

FOREIGN PATENT DOCUMENTS

| | | | |
|---|---|---|---|
| 1482092 | 3/1966 | France . | |
| 885007 | 12/1961 | United Kingdom . | |
| 1104818 | 2/1968 | United Kingdom | C07C 17/04 |

*Primary Examiner*—Alan Siegel

[57] ABSTRACT

A process for the preparation of perfluoroalkyl iodides, especially perfluoroethyl iodide, by reaction of perfluorinated compounds which contain a carbon carbon double bond with ICl in HF solvent in the presence of Lewis acid catalysts. The compounds are used as telogens for the telomerization of tetrafluoroethylene to long-chain perfluoroalkyl iodides.

19 Claims, No Drawings

LEWIS ACID CATALYZED CONJUGATED IODOFLUORINATION OF FLUOROOLEFINS

This is a continuation-in-part application of Ser. No. 08/099,679, filed on Jul. 29, 1993 now abandoned.

FIELD OF THE INVENTION

This invention concerns a process for the addition of the elements of iodine monofluoride across the carbon-carbon double bonds of olefins. The products herein are useful as telogens and/or organic intermediates.

TECHNICAL BACKGROUND

The addition of iodine monofluoride across carbon-carbon double bonds by reaction with ICl and HF in excess HF solvent in the presence of certain Lewis acid catalysts, leads to the preparation of fluoroiodo olefins. When the olefin is highly fluorinated or perfluorinated, the resulting product is a highly fluorinated or perfluorinated fluoroiodide. For example, when the process of the present invention is applied to tetrafluoroethylene (TFE) the product is perfluoroethyl iodide. Perfluoroethyl iodide and other perfluoroalkyl iodides are used as telogens for the telomerization of tetrafluoroethylene to long-chain perfluoroalkyl iodides. Telomerization is a free radical chemical reaction in which one or more molecules of a polymerizable substance (tetrafluoroethylene) combine with another molecule (perfluoroalkyl iodide) called the telogen. Perfluoroalkyl iodides are known compounds useful for making articles of commerce. Pentafluoroethyl iodide (PFEI) is a commercial product widely used as a telogen for preparation of long-chain perfluoroalkyl iodides.

When the reaction is applied to other olefins the fluoroiodo compounds that result are useful as telogens, as is perfluoroethyl iodide, or as intermediates in the syntheses of fluorocontaining organic compounds. For example, perfluoro methyl vinyl ether yields trifluoromethyl 2-iodotetrafluoroethyl ether which is useful as a telogen. Similarly, the process can be used to prepare other compounds of the type $RCFICF_2X$, where R is selected from the group consisting of F and $C_nF_{2n+1}$, n has a value of 1–10, X is selected from the group consisting of F and OR', and R' is perfluoroalkyl containing up to about 10 carbon atoms, branched or straight, optionally containing in-chain ether oxygen, and having F, $SO_2F$, COF, COCl or $CO_2CH_3$ as an end group, provided that when X is OR', R is F. The compounds where $SO_2F$ or $CO_2CH_3$ are the end groups are useful as organic intermediates or as telogens.

The known methods of preparation of PFEI and some other perfluoro alkyl iodides, are based on the reaction of $IF_5$ with a mixture of tetrafluoroethylene and iodine. Another method of preparation of PFEI is a two-step procedure, in which tetrafluorodiiodoethane is first prepared from tetrafluoroethylene and iodine and then converted to pentafluoroethyl iodide by reaction with iodine pentafluoride.

These processes have the disadvantage of requiring $IF_5$, which is prepared from elementary fluorine. Fluorine, as well as iodine pentafluoride, are substances dangerous to handle and expensive.

According to U.S. Pat. No. 3,829,512, PFEI can be prepared by the reaction of TFE or tetrafluorodiiodoethane with the mixture of $I_2/Cl_2$ and HF at temperatures of 50°–170° C. The reaction is catalyzed by antimony pentafluoride or other pentavalent antimony halides. No mention is made of the use of catalysts other than $SbX_5$ (X is halogen), or of operation at temperatures below 50° C.

SUMMARY OF THE INVENTION

This invention provides a process for the preparation of $RCFICF_2X$, where R is selected from the group consisting of F and $C_nF_{2n+1}$, n has a value of 1–10, X is selected from the group consisting of F and OR', and R' is perfluoroalkyl containing up to about 10 carbon atoms, branched or straight, optionally containing in-chain ether oxygen, and having F, $SO_2F$ or $CO_2CH_3$ as an end group, provided that when X is OR', R is F, which process comprises reacting a compound of the formula RCF=CFX, where R, X and n are as defined above, with an ICl/HF mixture in the presence of a Lewis acid catalyst which increases the Ho acidity of HF from −11 to at least −13, provided the Lewis acid catalyst is not an antimony compound, at a temperature of from about 0° to about 200° C.

DETAILED DESCRIPTION OF THE INVENTION

The process of the present invention concerns the preparation of perfluoroiodo compounds, especially perfluoroalkyl iodides, most especially perfluoroethyl iodide. Starting materials for the process comprise compounds of the general formula RCF=CFX, where R is selected from the group consisting of F and $C_nF_{2n+1}$, n has a value of 1–10, X is selected from the group consisting of F and OR'; and OR' is a perfluoroalkyl, branched or straight, containing up to about 10 carbon atoms, optionally containing one or more, preferably 1–5, more preferably 1 in-chain ether oxygen atoms, and having F, $SO_2F$ or $CO_2CH_3$ as an end group, provided that when X is OR', R is F. Preferred R substituents are $C_nF_{2n+1}$, where n is from 1 to 5, or fluorine. Most preferred is where R is fluorine.

Preferred X substituents are OR', where R' is a perfluoroalkyl wherein the alkyl moiety contains from 1 to 3 carbon atoms, or fluorine. Most preferred is where X is fluorine. Two more preferred compounds of the general formula RCF=CFX are $FSO_2CF_2CF_2OCF(CF_3)CF_2OCF=CF_2$ and $CH_3OC(O)CF_2CF_2OCF(CF_3)CF_2OCF=CF_2$. These latter compounds are useful as monomers in the preparation of highly fluorinated polymers.

The term "perfluoroalkyl" herein is defined as an alkyl compound in which the hydrogen atom that is directly attached to the carbon atoms is completely replaced by fluorine. In the term "perfluoroalkyl", the term "alkyl" denotes straight or branched alkyl such as methyl, ethyl, n-propyl, isopropyl, and the different butyl, pentyl, hexyl, heptyl, octyl, nonyl and decyl isomers.

The perfluoroalkyls of the R' designation optionally contain in-chain ether oxygen. For example $CF_3OCF_2CF_2$, $CF_3CF_2OCF(CF_3)CF_2$—, and $CF_3CF_2CF_2OCF(CF_3)CF_2OCF_2CF_2$—.

The iodine monochloride reagent, ICl, may be used as such or prepared in situ from equimolar amounts of iodine and chlorine as described in "Synthesis of Fluoroorganic Compounds," edited by L. Knunyants and G. G. Yakbson, Springer-Verlag, Berlin, 1985. HF serves as a solvent as well as a reagent. It dissolves ICl and at least partially dissolves the olefinic starting material. The proportion of ICl used is 0.01–1 mole per mole of HF, preferably 0.03–0.07 mole, and the ratio of ICl to olefin is preferably 1:1.

The Lewis acid catalyst is selected from the group of Lewis acid catalysts capable of enhancing the acidity, as measured by the Ho value, of hydrofluoric acid from its value of −11 to −13 or less. The acidity function, $H_o$, is defined as in the monograph "Superacids," G. A. Olah, G. K. S. Prakash and J. Sommer, pages 1–10, John Wiley and Sons, New York, 1985. This acidity enhancement is necessary to avoid the alternate reaction available to ICl of direct addition of ICl across the olefinic double bond to yield products of the type RCFClCFXI or RCFICF$_2$Cl which are undesirable impurities in the preparation of RCFICF$_2$X. Lewis acids suitable for this invention include boron trifluoride, niobium pentafluoride, tantalum pentafluoride, and bismuth pentafluoride, preferably boron trifluoride, niobium pentafluoride and tantalum pentafluoride; more preferably boron trifluoride and niobium pentafluoride. The most preferred Lewis acid catalyst is boron trifluoride. Other metal derivatives such as oxides, chlorides and alkoxides, which can be converted into fluorides under reaction conditions in HF, and which give appropriate H$_o$ acidities, can be employed.

None of the preferred or more preferred Lewis acid catalysts suffer from the inherent problems related to toxicity and waste disposal problems characteristic of antimony compounds.

Comparative Examples A, B and C show the effect of using no catalyst and using catalysts that do not meet the H$_o$ acidity requirement. Aluminum chloride and zinc chloride do not improve the yield over control experiments with no catalyst.

The proportion of the catalyst used may be from 0.0001 mole to 10 mole per mole HF, preferably 0.05–1. It is possible to use a higher ratio, but this results in only a slight yield increase. Compared to the pentavalent antimony compounds, boron trifluoride offers cleaner conversions, i.e., fewer side reactions due to the fact that pentavalent antimony compounds can also function as oxidation agents in addition to their being Lewis acids. No reaction residues remain when BF$_3$ is used and any waste or byproducts are less toxic and easier to treat or dispose of as opposed to reaction residues obtained with the use of heavy metal antimony compounds.

The reaction can be carried out conveniently at temperatures of from 0° to 200° C. Preferably, the reaction is carried out at temperatures from 20° to 100° C.

The reaction can be carried out in batch, semi-batch, semi-continuous or continuous modes in one or in a plurality of reaction vessels. On a laboratory scale, the reaction can be carried out in shaker tubes, where all reagents are combined before the reaction vessel is sealed and the reaction commenced. It can also be carried out in agitated autoclaves where all reactants except the olefin are combined and the olefin is fed in a controlled manner.

In the case where pentafluoroethyl iodide (PFEI) is the desired product, PFEI can be easily separated from HF by distillation allowing reuse of the HF and Lewis acid catalyst in subsequent preparations.

Agitation during the course of the reaction is preferred. Agitation can be carried out in any of the commonly used methods including stirring, shaking, and reagent introduction.

The proportion of HF used is from 2 to 40 moles per mole of olefin, preferably 5–25 mole.

Product may be isolated by any of the methods customary in organic synthetic chemistry. Fractional distillation is usually employed with liquid products. It is convenient to contact the reaction mixture with water prior to product isolation to extract ICl, HF and catalyst.

Pressure is not usually a critical variable. The reaction is typically carried out at 1 to 100 atmospheres pressure. It is convenient to start out below 1 atmosphere and to allow evolved HCl to build up the pressure in the reaction vessel. Reaction time can vary from several minutes to several hours, depending on such variables as catalyst concentration, pressure, and temperature.

EXAMPLES

GENERAL PROCEDURES

Olefins are commercial grade materials and are used as obtained. Tetrafluoroethylene and hexafluoropropene are obtained from PCR, Inc. in Gainsville, Fla. Hydrofluoric acid anhydrous, 99.5% is obtained from Allied Signal. Lewis acid catalysts are common laboratory grade materials. Iodine monochloride is purchased from Aldrich Chemical Co., Milwaukee, Wis.

Example 1

Preparation of Pentafluoroethyl Iodide

A 400 mL Hastelloy shaker tube was loaded with 48 g (0.3 mole) of ICl, evacuated, cooled down to −30° C. and then charged with 100 g (5 mole) of anhydrous HF, 5 g (0.074 mole) BF$_3$ and 30 g (0.3 mole) of tetrafluoroethylene (TFE). The reaction vessel was shaken 8 h at 50° C. and 10 h at 20° C. The gaseous products were then bled from the reaction vessel at 25°–40° C. These gases containing HCl, HF, and pentafluoroethyl iodide (PFEI) were passed through a washing vessel containing 1000 mL of water to remove the HF and HCl, and the product was collected in a cooled trap (−78° C.). Distillation of crude product through a low temperature column gave 57 g (78%) of PFEI with b.p. 11°–13° C.; 99% purity, according to GC and NMR $^{19}$F. The residue in the distillation pot, 3.5 g, was according to GC and NMR data, a mixture of 80% of PFEI and 20% CF$_2$Cl CF$_2$I (calculated yield 1%).

Example 2

Preparation of Pentafluoroethyl Iodide

Following the procedure described in Example 1, 10 g (0.147 mole) BF$_3$ was used. The reaction vessel was shaken 18 h at 20° C. The reaction mixture was worked up as described. The yield of PFEI was 91% the yield of CF$_2$Cl CF$_2$I was <1%.

Example 3

Preparation of Pentafluoroethyl Iodide

Following the procedure described in Example 1, 2 g (0.011M) NbF$_5$ was used in place of the boron trifluoride. The reaction vessel was shaken 8 h at 5° C. and 10 h at 20° C. . The yield of PFEI was 86%; the yield of CF$_2$ClCF$_2$I was <1%.

Example 4

Preparation of Pentafluoroethyl Iodide

Following the procedure described in Example 1, 1.15 g (0.006 mole) of TaF$_5$ was used in place of the boron trifluoride. The reaction vessel was shaken 8 h at 50° C. and 10 h at 20° C. The yield of PFEI was 53%; the yield of CF$_2$ClCF$_2$I was 9%.

Example 5

Preparation of Pentafluoroethyl Iodide

Following the procedure described in Example 1, 2 g (0.0065M) of $BiF_5$ was used in place of the boron trifluoride. The reaction vessel was shaken 18 h at 40° C. The yield of PFEI was 24%, the yield of $CF_2ClCF_2I$ was 12%.

Example 6

Preparation of 2-Iodoheptafluoropropane

Following the procedure described in Example 1, 10 g (0.147M) $BF_3$ and 45 g (0.3M) of hexafluoropropene (in place of TFE) were used. The reaction vessel was shaken 18 h at 50° C. The product was isolated as above. After distillation the yield of $(CF_3)_2CFI$ that was isolated was 70 g (79% yield) of purity >98%, GC, NMR. The boiling point was 37°–38° C.

Example 7

Preparation of $ICF_2CF_2OCF_3$

Following the procedure described in Example 1, 10 g (0.147M) $BF_3$ and 50 g (0.3M) of perfluoromethylvinyl ether were used. The reaction vessel was shaken 18 h at 50° C. The product was isolated as above. After distillation, 79 g (84%) of $ICF_2CF_2OCF_3$, b.p. 43°–44° C. were obtained.

Example 8

Preparation of $ICF_2CF_2OCF_2CF_2CF_3$

Following the procedure described in Example 1, 10 g (0.147M) $BF_3$ and 78 g (0.3M) of perfluoro-n-propylvinyl ether were used. The reaction vessel was shaken 18 h at 70° C. The product was isolated as above. After distillation, 101 g (82%) of $ICF_2CF_2OCF_2CF_2CF_3$, b.p. 84°–85° C. were obtained.

Example 9

Preparation of Pentafluoroethyl Iodide

A 1000 mL Hastelloy autoclave with stirrer is charged with 78 g (0.48 mole) of ICl, evacuated, cooled down to −30° C. and then charged with 225 g (11.25 mole) of anhydrous HF, 0.11 mole of $BF_3$, and 40 g (0.4 mole) of TFE. The reaction mixture is stirred at 40° C. for 8 h and then 10 h at 20° C. The gaseous products are then bled from the reaction vessel at 20° C. These gases are passed through a washing vessel containing 1500 mL of water and the product is collected in a cooled trap (−78° C.). The autoclave is then recharged with the same amount of ICl and TFE and the reaction is repeated under the same conditions. Four cycles are made in total. After the fourth run, the autoclave is completely discharged, as described above, at 40° C. The total yield of PFEI is about 299 g (68% yield).

Example 10

Preparation of $FSO_2CF_2CF_2OCF(CF_3)CF_2OCF_2CF_2I$

Following the procedure described in Example 1, 4 g (0.059M) $BF_3$, 45 g (0.1M) of $FSO_2CF_2CF_2OCF(CF_3)CF_2OCF=CF_2$, 16 g (0.1M) of ICl and 50 g of HF were used. After 18 h at 70° C., 200 ml of water was injected into the shaker tube to dilute the HF. The product (lower layer) was separated, washed twice with water, dried over $P_2O_5$ and distilled giving 49 g (82%) of $FSO_2CF_2CF_2OCF(CF_3)CF_2OCF_2CF_2I$, b.p. 130°–132° C./200 mm Hg.

COMPARATIVE EXAMPLES

Comparative Example

Reaction Without Catalyst

Following the procedure described in Example 1, 47 g (0.29 mol) of ICl, 30 g (0.3 mol) TFE, 100 g of HF was used. After 16 h at 25° C. the product was isolated as above. The yield of $C_2F_5I$ was 19%; the yield of $ClCF_2CF_2I$ was 48%.

Comparative Example B

Aluminum Chloride Catalyst

Following the procedure described in Example 1, 24 g (0.15 mol) ICl, 15 g (0.15 mol) of TFE, 1.5 g (0.011 mol) of $AlCl_3$ and 100 g of HF was used. The yield of $C_2F_5I$ was 11.5%; the yield of $CF_2ClCF_2I$ was 36%.

Comparative Example C

Zinc Chloride Catalyst

Following the procedure described in Example 1, 48 g (0.3 mol) ICl, 30 g (0.3 mol) of TFE, 1.5 g (0.011 mol) of $ZnCl_2$ and 100 g of HF was used. The reaction vessel was shaken 16 h at 25° C. The yield of $C_2F_5I$ was 13%; the yield of $CF_2Cl_2CF_2I$ was 49%.

What is claimed is:

1. A process for the preparation of $RCFICF_2X$ wherein R is selected from the group consisting of F and $C_nF_{2n+1}$, n has a value of 1–10, X is selected from the group consisting of F and OR', and R' is a perfluoroalkyl containing up to about 10 carbon atoms, branched or straight, optionally containing in-chain ether oxygen, and having F, $SO_2F$, or $CO_2CH_3$ as an end group, provided that when X is OR', R is F, which process comprises reacting a compound of the formula $RCF=CFX$ where R, X and n are as defined above, with an ICl/HF mixture in the presence of a Lewis acid catalyst which increases the Ho acidity of HF of −11 to at least −13, at a temperature of from about 0° to about 200° C., wherein the Lewis acid catalyst is selected from the group consisting of $BF_3$, $TaF_5$ and $NbF_5$, and wherein the yield of $RCFICF_2X$ product is at least 50%.

2. A process according to claim 1 wherein R is $C_nF_{2n+1}$ and n is 1–5.

3. A process according to claim 2 wherein X is OR' and R' is a perfluoroalkyl wherein the alkyl moiety contains from 1–3 carbon atoms.

4. A process according to claim 1 wherein R is F.

5. A process according to claim 1 wherein the molar proportion of ICl to HF is from 0.01 to 1.

6. A process according to claim 1 wherein the ratio of ICl to TFE is 1:1.

7. A process to claim 1 wherein the molar proportion of HF to TFE is 5 to 15.

8. A process according to claim 1 wherein the Lewis acid catalyst is selected from the group consisting of $BF_3$ and $NbF_5$.

9. A process according to claim 8 wherein the Lewis acid catalyst is $BF_3$.

10. A process according to claim 1 wherein the compound of the formula RCF=CRX is RCF=$CF_2$.

11. A process according to claim 1 wherein the RCF=CFX is $FSO_2CF_2CF_2OCF(CF_3)CF_2OCF$=$CF_2$.

12. A process according to claim 1 wherein the RCF=CFX is $CH_3OC(=O)CF_2CF_2OCF(CF_3)CF_2OCF$=$CF_2$.

13. A process according to claim 9 wherein the compound of the formula RCF=CFX is RCF=CROR' wherein R' is a perfluoroalkyl wherein the alkyl moiety contains from 1–3 carbon atoms.

14. A process according to claims 1 where the ICl/HF mixture is formed by mixing $I_2$, $Cl_2$ and HF.

15. The process of claim 1 carried out at a temperature of about 20° C. to about 100° C.

16. A process for the preparation of $C_2F_5I$ comprising reacting tetrafluoroethylene with ICl/HF mixture in the presence of $BF_3$.

17. A process for the preparation of $ICF_2CF_2OCF_3$ comprising reacting perfluoro-methyl vinyl ether with ICl/HF in the presence of $BF_3$.

18. A process for the preparation of $ICF_2CF_2OCF_2CF_2CF_3$ comprising reacting perfluoro-n-propylvinyl ether with ICl/HF mixture in the presence of $BF_3$.

19. A process for the preparation of $RCFICF_2X$ wherein R is selected from the group consisting of F and $CnF_{2n+1}$, n has a value of 1–10, X is selected from the group consisting of F and OR', and R' is a perfluoroalkyl containing up to about 10 carbon atoms, branched or straight, optionally containing -n-chain ether oxygen, and having F, $SO_2F$, or $CO_2CH_3$ as an end group, provided that when X is OR', R is F, which process comprises reacting a compound of the formula RCF=CFX where R, X and n are as defined above, with an ICl/HF mixture in the presence of a $BF_3$ Lewis acid catalyst which increases the —Ho acidity of HF of 11 to at least 13 and and wherein the yield of $RCFICF_2X$ product is at least 60%.

* * * * *